United States Patent [19]

Nagy et al.

[11] Patent Number: 5,312,622
[45] Date of Patent: May 17, 1994

[54] ACARICIDAL COMPOSITIONS AND PROCESS FOR PREPARING SAME

[75] Inventors: Tibor Nagy; Karoly Zalai; Dénes Máthé; Béla Stefkó, all of Budapest; Arpád Hadházy, Szekszárd; Gyula Csókás, Tamási; István Gebhardt, Budapest, all of Hungary

[73] Assignee: Richter Gedeon Vegyeszeti Gyar Rt., Budapest, Hungary

[21] Appl. No.: 828,870
[22] PCT Filed: Jun. 25, 1990
[86] PCT No.: PCT/HU90/00042
§ 371 Date: Jan. 30, 1992
§ 102(e) Date: Jan. 30, 1992
[87] PCT Pub. No.: WO91/00013
PCT Pub. Date: Jan. 10, 1991
[51] Int. Cl.$^5$ .............................. C12N 1/20
[52] U.S. Cl. ....................... 424/93 K; 424/93 N; 424/93 C
[58] Field of Search ............... 424/93 K, 93 N, 93 C

[56] References Cited

PUBLICATIONS

Bergy's Manual of Determinative Bacteriology, Eighth Ed; R. E. Buchanan et al, p. 226, Williams and Wilkins, 1974.
The Prokaryotes, A Handbook on Habitats, Isolation and Identification, of Bacteria, Mortimer P. Starr et al, vol. I, p. 689, Springer-Verlag (1981).

Primary Examiner—Douglas W. Robinson
Assistant Examiner—Jean C. Witz
Attorney, Agent, or Firm—Herbert Dubno; Jonathan Myers

[57] ABSTRACT

The invention relates to acaricidal compositions containing as active ingredient: the fermentation broth or cell-free fermentation broth, of a concentrate of the fermentation broth or cell-free fermentation broth, or a solidified form of the fermentation broth or cell-free fermentation broth of one or two bacterium strains deposited at the National Collection of Agricultural and Industrial Microorganisms, Budapest, Hungary under the identification Nos. 001083 and 001086 or of their mixed micropopulation, if desired, in a sterilized state, optionally together with the metabolism products arising during the fermentation and inutilized nutriments, as well as one or more solid and/or liquid carrier(s) (preferably sugar or a grist of natural minerals), or an inert solvent (e.g. water) and, if desired, with surface active (preferably anionic or nonionic emulsifying or dispersing) agents. The compositions according to the invention can be used for protecting *Apis mellifera* (honey bee) against mites, particularly *Varroa jacobsoni*.

9 Claims, No Drawings

ACARICIDAL COMPOSITIONS AND PROCESS FOR PREPARING SAME

FIELD OF THE INVENTION

The invention relates to acaricidal compositions containing as active ingredient the fermentation broth of one of two bacterium strains deposited at the National Collection of Agricultural and Industrial Microorganisms, Budapest, Hungary (hereinafter abbreviated: NCAIM) under the identification Nos. 001083 and 001086 on May 25, 1989, or the fermentation broth of their mixed micropopulation. The invention further relates to the cell-free fermentation broth of said bacterium strains or a concentrate of the cell-free or non cell-free fermentation broth thereof or a solidified form of the cell-free or non cell-free fermentation broth thereof, which may be in a sterilized form, optionally together (in admixture) with additive(s). The invention further relates to a process for the preparation of both strains and their mixed micropopulation.

The invention also relates to the bacillus strain deposited at NCAIM under the identification No. 001083 and the mixed micropopulation of both strains, respectively.

The invention further relates to the agricultural use of both bacterium strains or their mixed micropopulation.

From the two bacteria mentioned above, the bacillus strain deposited at NCAIM under the identification No. 001083 is novel whereas the pseudomonas deposited under the identification No. 001086 is known. The mixed microA4635-67-TF/KmO population of both bacteria is also novel.

The composition according to the invention is used e.g. for protection against parasitic mites living on *Apis mellifera* (honey-bee), preferably against *Varroa jacobsoni* mites (against varroatosis).

BACKGROUND OF THE INVENTION

It is known that *Varroa jacobsoni* is a mite parasitically living on *Apis mellifera* and which usually sucks at the faeces of bee-grubs by its sucking mandible and the pellicle of the pupae; but most willingly, it taps the haemolymph of the growing bees. As a result of the infection and in proportion thereto various distortioned evolution forms appear, the bees become weakened, become susceptible to other diseases and finally they perish.

The infection spreads to all important melliferious areas causing substantial losses. After the first infection, such losses appear in a surge-like manner, at the beginning in every third and fourth year and later in every second or third year. The death of the bee colony resembles an intoxication in most cases.

Several ways of protection against varroatosis are known:

1) Treatment or fumigation, respectively of the bee hives with various ethereal oils;

2) Application of various synthetic organic active agents, e.g.:
 a synergistic combination of pyrethrin with piperonylbutoxide [see in: Chemical Abstracts World Patent Index (hereinafter: WPI) Acc. No. 86-212705/337;
 a combination containing tetradifon [the Pesticide Manual 8th Ed., the British Crop Protection Council, Registry Number (hereinafter: Reg. No.) 116-29-07 and dicofol (Reg. No. 115-32-2) (WPI Acc. No. 86-037330/06);
 bee wax containing an antiparasitic active agent, e.g. isopropyl 4,4'-dibromo-benzylate (WPI Acc. No. 85-290439/47);
 1-pyridylformimino-2-phenoxymethyl-2-imidazoline derivatives (WPI Acc. No. 85-224091/37);
 2-anilinomethyl-2-imidazoline derivatives (WPI Acc. No. 85-217891/36);
 2-dimethylphenylimino-3-methylthiazoline (WPI Acc. No. 84-284115/46);
 compositions containing azoxybenzene (WPI Acc. No. 82-95526E/45);
 acetone solution of an aryl N-methylcarbamate (WPI Acc. No. 78-82396A/46); and
 foods and drinking water containing synthetic pyrethroids (WPI Acc. No. 87.130028/19).

Compositions containing synthetic organic active ingredients are applied by dusting (atomizing) or fumigation on the hives. Such commercialized compositions (which have, however, not been authorized in all countries) are e.g. Mitac EC (200 g/l) and Mitac WP (250–500 g/kg) containing amitrase as active ingredient; and Ectodex EC (50 g/l) (The Pesticide Manual 8th Ed., 1987; The British Crop. Protection Council, entry number 330). Their use is possible only at an appropriate external temperature (above 10° C.).

According to some suppositions, in the case of treatments carried out at the wrong time or with too high a frequency, damaging side products can be accumulated in the honey which may be harmful to both the beekeeper and the honey as well.

3) Use of attracting and repelling agents (attractants and repellents):
 WPI Acc. No. 87-129545/19 and
 WPI Acc. No. 84-018266/04;

4) Other methods of protection, e.g.
 mechanical protection (WPI Acc. No. 84-302720/49) and
 sterilization of the mites by X rays (WPI Acc. No. 86-048673/08).

SUMMARY OF THE INVENTION

During our investigations aimed at the protection of bees against mites it has been found that the fermentation broth of one or two bacterium strains deposited at NCAIM under the identification Nos. 001083 and 001086 or the fermentation broth of their mixed micropopulation, optionally the cell-free fermentation broth thereof or a concentrate of the cell-free or non cell-free fermentation broth thereof or a solidified form of the fermentation broth or cell-free fermentation broth (dried powder of the fermentation broth) thereof are very effective against varroatosis.

This effect is very definite if the acaricidal compositions according to the invention (see examples 4–12) are used before wintering. In addition, their toxicity is about one twentieth in comparison to that of the commercially available amitrase and, moreover, in the case of feeding and watering the bees using the new compositions an effect of 100% was observed. This fact has an outstanding importance because the feeding or watering can be carried out in a remarkably simple way. Using this type of administration the normal way of life of the bee-families need not be disturbed by fumigation or by dismembering the hives. Moreover, as it is shown in example 38, an effect of 100% could not be achieved by the widespread amitrase-treating.

The importance of the entirely new compositions according to our invention is underlined by those observations that more and more traditional acaricidal agents must be used to obtain the same result, which means, that a certain by the mites can be observed.

Moreover the present invention is surprising since up to the present no protection against mites has been achieved by using a fermentation broth in any form.

Thus, the present invention relates to an acaricidal composition, which comprises as active ingredient
the fermentation broth or cell-free fermentation broth, or
a concentrate of the fermentation broth or cell-free fermentation broth, or
a solidified form of the fermentation broth or cell-free fermentation broth of one or two bacterium strains deposited at the National Collection of Agricultural and Industrial Microorganisms, Budapest, Hungary under the identification Nos. 001083 and 001086 or of their mixed micropopulation, if desired, in a sterilized state, optionally together with the metabolism products arising during the fermentation and inutilized nutriments, as well as one or more solid and/or liquid carrier(s) (preferably sugar or a grist of natural minerals), or an inert solvent (e.g. water) and, if desired, with surface active (preferably anionic or nonionic emulsifying or dispersing) agents.

The invention further relates to the bacillus strain deposited at NCAIM under the identification No. 001083 or its mixed micropopulation with pseudomonas bacterium deposited at NCAIM under identification No. 001086, as well as to a process for the preparation and preservation (maintaining) of the bacillus strain.

The invention also relates to protection against mites, preferably *Varroa jacobsoni* parasitic mites, characterized by treating *Apis mellifera* or the hive or its frames or, of desired, feeding or watering *Apis mellifera* with a composition containing as active ingredient the fermentation broth of one or two bacterium strains deposited at NCAIM under the identification Nos. 001083 and 001086 or of their mixed micropopulation, optionally the cell-free fermentation broth thereof, or a concentrate of the cell-free or non cell-free fermentation broth thereof or a solidified form of the fermentation broth or cell-free fermentation broth thereof.

The bacterium (bacteria) according to the present invention are obtained by collecting a sample from a superficial layer (from a depth of 2 to 5 cm) of the soil. At least 3 samples are taken for each collection by sterile devices and transferred in air-tight bottles.

The strains are isolated from a few grams of soil by using the plate method in such a way that the soil sample is suspended in a nearly 100-fold volume of a physiological solution, suitably saline and then a serial dilution is prepared from the suspension by using physiological saline under constant stirring. An aliquot of this (e.g. 1 ml each) is pipetted into a sterile Petri-dish, about 10-fold volume of liquid nutritive medium (nutritive agar) of 40° to 45° C. temperature are added, thoroughly mixed and left to solidify.

The nutritive medium may be composed e.g. as follows:

| a) Meat extract | 3.0 g |
| Peptone | 10.0 g |
| Agar | 20.0 g |
| Distilled water | 1000.0 ml |
| pH = 7.2 | |
| Sterilization at 120° C. for 20 minutes; or | |
| b) Meat extract | 3.0 g |
| Peptone | 5.0 g |
| Agar | 15.0 g |
| Distilled water | 1000.0 ml |
| pH = 7.0 | |
| Sterilization at 120° C. for 20 minutes. | |

The Petri dishes are suitably turned downwards and then an incubation is carried out at 25° to 30° C. for a few (2 to 6) days.

During the incubation colonies appear on the nutrient medium. From these, the colonies are further processed, which are present in Petri dishes containing 10 to 20 colonies. These colonies are further propagated in themselves in a known manner. Thus, colonies containing a homogeneous micropopulation with the same morphological character, or a mixed micropopulation optionally developed spontaneously, respectively, are obtained.

The spontaneously developed mixed or the pure micropopulation are preserved (maintained) on a slant nutrient medium, suitable e.g. with the following composition:

| Meat extract | 1.0 g |
| --- | --- |
| Yeast extract | 2.0 g |
| Peptone | 5.0 g |
| Sodium chloride | 5.0 g |
| Agar | 15.0 g |
| Distilled water | 1000.0 ml |
| pH = 7.4 | |
| Sterilization at 121° C. for 15 minutes. | |

The freshly inoculated tubes are incubated at 32° C. for 48 hours and then suitably stored at 4° C. in a refrigerator.

The cells from the surface of the thus stored slant nutrient media are suspended in physiological saline and preferably inoculated onto a nutrient solution containing the following ingredients (components):

| Peptone | 7.8 g |
| --- | --- |
| Triton | 7.8 g |
| Yeast extract | 7.8 g |
| Sodium chloride | 5.6 g |
| Glucose | 1.0 g |
| Distilled water | 1000.0 ml |
| pH = 7.5 | |
| Sterilization at 120° C. for 20 minutes. | |

It is then subjected to fermentation, preferably in a shaken culture at 30° to 35° C. for 2 to 3 days, optionally by standing cultivation (in a partially anaerobic manner).

If desired, the fermentation broth is made cell-free in some way, preferably by membrane filtration. The biological, suitably the acaricidal effect of the fermentation broth or cell-free fermentation broth is investigated. The biologically effective, optionally mixed micropopulation is separated to its strain components.

In the latter case the mixed micropopulation is repeatedly propagated on a nutrient medium used for differential diagnostic purposes.

Suitable ingredients (components) of nutrient media used for differential diagnostics are e.g. as follows:

| a) Peptone | 20.0 g |
|---|---|
| Sodium chloride | 5.0 g |
| Agar | 15.0 g |
| Distilled water | 1000.0 ml |
| Defibrinated blood | 20-50 ml |

The nutrient medium is sterilized at 120° C. without adjusting the pH value for 20 minutes. Before pouring out it is cooled down to 48° C. and then 2 to 5% by volume of defibrinated blood are added under sterile conditions.

| b) Meat extract | 0.3 g |
|---|---|
| Peptone | 1.0 g |
| Agar | 2.0 g |
| Distilled water | 1000.0 ml |
| Sterile defibrinated blood | 10.0 ml |

The blood is poured into the nutrient medium previously molten and cooled to 48° C., then the mixture is placed into a water bath of 80° C. for 5 minutes. The nutrient medium is plated in sterile Petri dishes after 5 minutes.

| c) Meat extract | 5.0 g |
|---|---|
| Peptone | 10.0 g |
| Dextrose | 5.0 g |
| Disodium hydrogen phosphate | 4.0 g |
| Iron (II) sulfate (ferrous sulfate) | 0.3 g |
| Bismuth sulfite | 8.0 g |
| Brillant green | 0.025 g |
| Agar | 20.0 g |
| Distilled water | 1000.0 ml |
| pH = 7.7 | |

The solution containing all ingredients is heated under vigorous stirring until it foames up to the neck of the flask, then it is allowed to cool to 50°-55° C. under continuous stirring and poured into Petri dishes.

| d) Protease peptone | 10.0 g |
|---|---|
| Yeast extract | 3.0 g |
| Lactose | 10.0 g |
| Saccharose | 10.0 g |
| Sodium chloride | 5.0 g |
| Phenol red | 0.08 g |
| Brillant green | 0.0125 g |
| Agar | 12.0 g |
| Distilled water | 1000.0 ml |
| pH = 6.9 | |

The nutrient medium is sterilized at 120° C. for 15 minutes, then poured into sterile Petri dishes.

In this way a fermentation broth or its various forms (Examples 3 to 11) are obtained which are used directly or in the form of one of their compositions (Examples 12 to 37) for treating *Apis mellifera* infected by Varroa jacobsoni.

According to the invention, the active ingredient (including also the fermentation broth containing cells or its condensate, or the cell-free fermentation broth or its condensate, or the solid forms thereof optionally sterilized by irradiation are formulated in a known way to compositions dusting or wettable powders, such as suspension concentrates, aerosols, water-soluble concentrates or other compositions which are useful e.g. for feeding or watering. The formulation of these compositions is carried out in a manner known per se (Pesticide Formulations, edited by Wade van Valkenburg, Marcel Dekker Inc., New York 1973).

In these compositions the active ingredient is mixed with solid or liquid carriers, solvents, tensides and optionally with other auxiliary materials (additives) in order to make the active ingredient more useful for application (see e.g. the British patent specification No. 1,552,277).

The demand on these auxiliaries (additives) consists in that they should be nontoxic to the bees and indirectly to man.

The solid carriers or vehicles may be inorganic or organic and, on the other hand, native or artificial in character. Native solid carriers or vehicles can be obtained from various minerals (such as diatomaceous earth, bentonite, sorts of perlite, kaolinite, dolomite and the like) by grinding.

The artificial solid carriers or vehicles are e.g.: silicic acids with a great surface (aerosils); silica gels prepared by various methods; tinely distributed calcium carbonate obtained by neutralizing lime milk or the neutralized aluminum hydrate or its heat-treated derivatives obtained by grinding are also carriers of artificial origin.

As native solid organic carriers e.g. flour, sugar, grists of some plant wastes such as wood flour and the like may be used.

Suitable liquid carriers and solvents are water, various organic solvents and their mixtures; alkanols and polyhydric alkanols and their esters formed with various acids, e.g. fatty, aromatic, hydroxy or amino acids such as ethyl acetate, isobutyl acetate, amyl acetate, methyl benzoate, dioctyl phthalate and the like; though other polar organic solvents such as acid amides, e.g. dimethylformamide, lactones, e.g. gamma-butyrolactone and lactams, e.g. N-methylpyrrolidone may also be used to the same purpose.

The tensides (surface active agents) used in various compositions are meant in a broad sense: emulsifying, dispersing and wetting agents being commonly known in the formulation of pesticides belong to this type of additives.

The tensides may be nonionic or ionic in their character.

Nonionic tensides are e.g.: ethers of ethylene oxide formed with alcohols; esters of ethylene oxide formed with fatty acids or oleic acid; ethers of ethylene oxide formed with aralkylphenols; block polymers of ethylene oxide with propylene oxide; esters and ethers thereof; as well as derivatives of ethylene oxide formed with fatty acids or oleic acid and hexitol anhydrides such as e.g. nonylphenyl polyglycol ethers, polyroxyethylene oleate esters or polyoxyethylene sorbitan monooleate and the like.

The ionic tensides are anionic, cationic or amphoteric in their nature.

Anionic tensides are e.g.: various organic acids, e.g. carboxylic and sulfonic acids; sulfates and sulfonates of alcohols; phosphate esters of polyoxyethylene ethers and esters and their salts formed with an alkaline earth metal or with organic cations such as soft soap, calcium, sodium, ammonium or diisopropylammonium dodecylbenzenesulfonate; sodium diisooctylsulfosuccinate; or salts of the polyacrylic acid formed with the above cations.

Cationic tensides are e.g.: hydrohalides of the higher alkylamines or their sulfonates; stearyldimethylammonium chloride; or higher ethanolamines or their salts and optionally the salts formed with anionic tensides, too.

Amphoteric tensides are e.g. betains, lecithins or sodium N-methylalkyltaurimide and the like.

Useful additives, e.g. adhesives are the native or synthetic polymers such as e.g. starch, dextrin, mono- or disaccharides, carboxymethylcellulose, hydroxyethylcellulose, polyvinylpyrrolidone, polyacrylic acid, xanthane gum, alginates and the like.

Useful anti-foam agents are e.g. the polyoxyethylene-polyoxypropylene block polymerisates, higher alkanols or particular silicone oils.

Other additives, e.g. attractants such as honey, mono- or disaccharides and perfumes such as isoamyl acetate and the like may also be employed.

Additives (auxiliary materials) include also the stabilizers ensuring the microbiological stability of the composition. Useful stabilizers are e.g. benzoic acid, sodium benzoate, esters of 4-hydroxybenzoic acid and the like.

The active ingredient can be formulated to liquid, solid or aerosol form for the application (for the use).

For preparing liquid compositions, the active ingredient is dissolved or suspended in a suitable solvent (preferably in water) simultaneously with the additives mentioned above or by adding one additive after the other.

Liquid compositions may be either homogeneous or dispersed systems. These can be prepared by crushing (grinding) the solid active ingredient to the corresponding particle (grain) size, then homogenizing it with the dispersing medium optionally containing also the required surface active agents, by using a stirrer with a low revolution number, then further grinding e.g. in a pearl mill. To the suspension obtained an anti-foam agent and, if desired, viscosity-increasing materials are added under stirring with a low revolution number.

Dusting powders (dust compositions) may be prepared in such a way that the active ingredient is ground in a suitable equipment and then homogenized together with the carrier and the surface active agent. The above process may also be modified in such a manner that the active ingredient, carrier and surface active agent(s) are previously homogenized, then ground and finally again homogenized. Hammer mill, rod mill or air-jet mill may be used for the grinding. Dusting powders (dust compositions) may be prepared also in such a manner that the carrier and surface active agents are dispersed or dissolved in the dispersion or solution, respectively, containing the active ingredient, then the liquid thus obtained is brought into a solid form by using a known process such as spray-drying or lyophilization. If desired, the dust obtained is ground and then homogenized.

It desired to use such amounts (doses) of liquid compositions (e.g. fermentation broths), which do not hinder the free motion of *Apis mellifera* by wetting. In the case of e.g. the cell-free fermentation broth prepared according to Example 8a) this dose may be 5 to 500 ml/m² of bee frame. The dose, however, may be lower or higher than this value since the fermentation broths and their various forms are nontoxic to *Apis mellifera*. The frequency and dose of the treatments usually depend on the grade of infectedness.

Because of the drawback of the liquid compositions cited above, various powder-form compositions can be used with a greater advantage. The doses of the latter ones are usually between 0.01 and 10 g of active ingredient/m² of bee frame.

The feeding and drinking (watering) composition represent a very preferred application form ensuring the prolonged and uniform administration and making the opening of the hives unnecessary in opposition to various sprays and dusts. In this case, the duration of feeding and drinking (watering) may be defined, which in turn depend on the decrease in or eventually total eradication of the infection.

The invention is illustrated in detail by the following non limiting Examples.

EXAMPLE 1

Isolation of the strains

The microorganisms were isolated from forest soils (acacia forest of Tolna county, September 1986) by using the plate method. One gram of the soil sample was suspended in 99 ml of physiological sodium chloride (saline) solution and a serial dilution was prepared by adding 3 ml of suspension each to 27 ml of physiological saline in each dilution step. One ml from each flask was pipetted into an empty sterile Petri dish of 4 cm in diameter and 9 ml of molten liquid nutrient medium each of 40° to 45° C. containing 0.02 mg/ml of actidione were added.

By the elliptic movement of the Petri dish the suspension was thoroughly mixed with the agar and left to solidify. Then the Petri dishes were turned downwards and incubated at 28° C. for 72 hours.

For the further investigations those Petri dishes, containing a number between 10 and 20 of grown colonies, were used. These colonies were propagated several times in a known way to obtain nine morphologically homogeneous colonies being different from each other. Nine of these colonies were homogeneous whereas one was a spontaneously developed mixed micropopulation. The acaricidal effect of the fermentation broths or cell-free fermentation broths of the thus isolated pure or mixed micropopulations, respectively, which were prepared as described in Examples 3a) or 8a) or b), respectively, was studied according to Examples 38 to 40.

EXAMPLE 2

Isolation of the subcultures of spontaneously developed mixed micropopulations From the spontaneously developed mixed micropopulation two strains (pure subcultures) were isolated by repeated propagation on a solid nutrient medium used for differential diagnostics (chocolate agar, bloody agar, brilliant green agar, bismuth sulfite agar and the like) and by ageing of the cultures. Both strains were deposited at NCAIM under the identification Nos. 001083 and 001086. One of these strains is a novel bacillus; the other one is known, belongs to the pseudomonas genus and possesses the following bacteriological features:

a) The pseudomonas strain deposited under the identification No. 001086 forms shiny colonies of 0.5 to 1 mm in diameter on simple nutrient agar, shows a weak growth at 37° C. and a better growth at 30° C.

b) The bacillus strain deposited under the identification No. 001083 forms mat greyish colonies of 1 to 2 mm in diameter on simple nutrient agar.

| | |
|---|---|
| a) Gram: | positive, |
| b) sporulation: | oval, |
| c) motion: | positive, |
| d) anaerobic growth: | positive, |

-continued

| | | |
|---|---|---|
| e) growth on bismuth sulfite agar: | | +/−, |
| f) growth on eosin-methylene blue aqar: | | +/−, |
| g) growth in the presence of 7% sodium chloride: | | positive, |
| h) catalase: | | positive, |
| i) $NO_3 \rightarrow NO_2$: | | negative, |
| j) Voges-Proskauer test | | negative, |
| k) indole: | | negative, |
| l) urease (kristensen): | | negative, |
| m) arginine-dihydrolase: | | negative, |
| n) lysine-decarboxylase: | | negative, |
| o) ornithine-decarboxylase: | | negative, |
| p) aesculin hydrolysis: | | positive, |
| q) starch hydrolysis: | | negative, |
| r) casein hydrolysis: | | negative, |
| s) lecithin hydrolysis: | | negative, |
| t) gelatine hydrolysis: | | positive, |
| u) ammonium citrate: | | negative, |
| ü) acid formation on the Hungh-Leifson's oxidation-fermentation nutrient medium: | | oxidative, |
| v) gas formation, peptone-water glucose: | | negative, |
| x) acid formation (BSS) | glucose: | positive, |
| | fructose: | positive, |
| | lactose: | negative, |
| | maltose: | negative, |
| | mannitol: | positive, |
| | rhamnose: | negative, |
| | saccharose: | positive, |
| (peptone water) | arabinose: | negative, |
| | adonitol: | negative, |
| z) ONPG: | | positive. |

EXAMPLE 3

Fermentation of the pure bacterium strains deposited at NCAIM under the identification Nos. 001083 and 001086 characterized in Example 2 or their spontaneously developed mixed micropopulation, respectively a) The cells of the mixed micropopulation preserved (maintained) on slant nutrient medium were suspended in 5 ml of physiological saline each in a tube and 1 ml of this suspension each was inoculated to 100 ml of a nutrient solution each sterilized at 120° C. for 20 minutes which had been placed in a 500-ml flask and contained the following ingredients (components).

| | |
|---|---|
| peptone | 0.78% |
| triton | 0.78% |
| yeast extract | 0.78% |
| sodium chloride | 0.56% |
| glucose | 0.1% |
| pH = 7.5 | |

After inoculation the flasks were shaken at 32° C. with 200 rpm for 72 hours.

b) The process described under a) was followed, except that the pure pseudomonas bacterium strain deposited at NCAIM under the identification No. 001086 was subjected to fermentation.

EXAMPLE 4

Fermentation and subsequent spray-drying (drying by atomization) of the spontaneously developed mixed micropopulation of bacterium strains deposited at NCAIM under the identification Nos. 001083 and 001086 characterized in Example 2

One liter of the fermentation broth according to Example 3 a) which contained 2.4% of dry substance, was spray-dried (dried by atomization) by using air with an inlet temperature of 120° C. and outlet temperature of 65° to 75° C. to obtain 25.5 g of dry product with a moisture content of 5.8%.

EXAMPLE 5

Fermentation, subsequent spray-drying (drying by atomization) and X ray sterilization of the spontaneously developed mixed micropopulation of bacterium strains deposited at NCAIM under the identification Nos. 001083 and 001086 characterized in Example 2

The product obtained as described in Example 4 was irradiated with a 5 KGr dose of gamma-rays.

The effectiveness of the irradiating sterilization was controlled by using the plate method in a known manner.

EXAMPLE 6

Fermentation and subsequent lyophilization of the spontaneously developed mixed micropopulation of the bacterium strains deposited at NCAIM under the identification Nos. 001083 and 001086 characterized in Example 2

100 ml of the fermentation broth each obtained according to Example 3 a) were maintained at −25° C. for 24 hours and then lyophilized in an Edwards Supermodulyo 12K type apparatus for 24 hours to obtain 2.3 to 2.5 g of lyophilized product each.

EXAMPLE 7

Fermentation, subsequent lyophilization and irradiating sterilization of the spontaneously developed mixed micropopulation of the bacterium strains deposited at NCAIM under the identification Nos. 001083 and 001086 characterized in Example 2

The lyophilized product obtained in Example 6 was irradiated by 5 KGr dose of gamma-rays.

The effectiveness of the irradiating sterilization was controlled by using the plate method in a known manner.

EXAMPLE 8

Fermentation and subsequent removal of cells in the case of the pure bacterium strains deposited at NCAIM under the identification Nos. 001083 and 001086 characterized in Example 2 or their spontaneously developed mixed micropopulation, respectively a) One liter of the fermentation broth containing the mixed micropopulation according to Example 3 a) was centrifuged on a LU 418H type cooled centrifuge at 4000 rpm for 1 hour at 4° C. The cells were completely removed by repeated filtration of the supernatant through a Sartorius membrane of 0.45 and then 0.2 μm pore size. The fermentation broth thus treated contained 1.02% of dry substance.

The effectiveness of cell removal was controlled by using the plate method in a known way.

b) The process described under a) was followed, except that the fermentation broth of the pseudomonas deposited at NCAIM under the identification No. 001086 was made free from cells.

EXAMPLE 9

Fermentation of, subsequent cell removal from and spray-drying of the spontaneously developed mixed micropopulation of the bacterium strains deposited at NCAIM under the identification Nos. 001083 and 001086 characterized in Example 2

One liter of the fermentation broth described in Example 8 a), which contained 1.02% of dry substance, was dried by using air with 120° C. inlet temperature and 65° to 75° C. outlet temperature. In this way 10.57 g of product containing 3.7% of moisture were obtained.

EXAMPLE 10

Fermentation of, subsequent cell removal from and lyophilization of the spontaneously developed mixed micropopulation of the bacterium strains deposited at NCAIM under the identification Nos. 001083 and 001086 characterized in Example 2

One liter of the fermentation broth described in Example 8 a) was maintained at −25° C. for 48 hours and lyophilized in an Edwards Supermodulyo 12K type apparatus during 24 hours to give 10.2 g of lyophilized product.

EXAMPLE 11

Fermentation of, subsequent cell removal from and film evaporation of the spontaneously developed mixed micropopulation of the bacterium strains deposited at NCAIM under the identification Nos. 001083 and 001086 characterized in Example 2

One liter of the fermentation broth described in Example 8 a) was evaporated to a volume of 0.33 liter at 50° C. under a reduced pressure of 380 Hgmm in a film evaporator.

EXAMPLE 12

Fermentation of, cell removal from, adding 1/60 part by weight of saccharose to the fermentation broth obtained and lyophilization of the spontaneously developed mixed micropopulation of the bacterium strains deposited at NCAIM under the identification Nos. 001083 and 001086 characterized in Example 2

1/60 part by weight of saccharose was added to 1 liter of the fermentation broth described in Example 8 a), the broth was maintained at −25° C. for 48 hours and lyophilized in an Edwards Supermodulyo 12K type apparatus over 24 hours.

Liquid Compositions

Sprays (spraying compositions)

EXAMPLE 13

| | |
|---|---|
| Active ingredient according to Example 3 a) or b), respectively | 99.8% |
| Polyoxyethylene sorbitan monooleate | 0.1% |
| 10% emulsion of methylsilicone oil | 0.1% |

The composition is obtained by mixing (homogenizing) the components.

EXAMPLE 14

| | |
|---|---|
| Active Ingredient according to Example 8 a) | 97.8% |
| Dextrin | 2.0% |
| Polyoxyethylene sorbitan monooleate | 0.1% |
| 10% emulsion of methylsilicone oil | 0.1% |

The composition is prepared as described in Example 13.

EXAMPLE 15

| | |
|---|---|
| Active ingredient according to Example 11 | 92.0% |
| Saccharose | 7.2% |
| Polyoxyethylene sorbitan monooleate | 0.5% |
| 10% emulsion of methylsilicone oil | 0.3% |

The composition is prepared as described in Example 13.

EXAMPLE 16

| | |
|---|---|
| Active ingredient according to Example 11 | 93.0% |
| Saccharose | 6.3% |
| Fatty alcohol polyoxyethylene ether phosphate ester potassium salt | 0.25% |
| Polyoxyethylene sorbitan monooleate | 0.15% |
| 10% emulsion of methylsilicone oil | 0.25% |
| Isoamyl acetate | 0.05% |

The composition is obtained as described in Example 13.

EXAMPLE 17

| | |
|---|---|
| Active ingredient according to Example 3 a) or b), respectively | 99.7% |
| Polyoxyethylene sorbitan monooleate | 0.1% |
| 10% emulsion of methylsilicone oil | 0.1% |
| Xanthane gum | 0.1% |

The composition is obtained as described in Example 13.

EXAMPLE 18

| | |
|---|---|
| Active ingredient according to Example 4 | 30.0% |
| Polyoxyethylene sorbitan monooleate | 1.0% |
| Saccharose | 10.0% |
| 10% emulsion of methylsilicone oil | 0.5% |
| Water | 58.0% |
| Isoamyl acetate | 0.5% |

The composition is obtained as described in Example 13.

EXAMPLE 19

| | |
|---|---|
| Active ingredient according to Example 5 | 30.0% |
| Polyoxyethylene sorbitan monooleate | 1.0% |
| Saccharose | 10.0% |
| 10% emulsion of methylsilicone oil | 0.5% |
| Water | 58.0% |
| Isoamyl acetate | 0.5% |

The composition is obtained as described in Example 13.

EXAMPLE 20

| | |
|---|---|
| Active ingredient according to Example 11 | 93.0% |
| Saccharose | 6.4% |
| Fatty alcohol polyoxyethylene ether phosphate ester | 0.25% |
| Polyoxyethylene sorbitan monooleate | 0.15% |
| Lecithin | 0.15% |
| Isoamyl acetate | 0.05% |

The composition is obtained as described in Example 13.

Compositions useful for feeding

EXAMPLE 21

| Active ingredient according to Example 8 b) | 79.95% |
|---|---|
| Saccharose | 20.0% |
| Isoamyl acetate | 0.025% |
| Ethyl acetate | 0.025% |

The composition is prepared by mixing the components.

EXAMPLE 22

| Active ingredient according to Example 8 b) | 50.0% |
|---|---|
| Mixed nectar | 50.0% |

The composition is prepared as described in Example 21.

EXAMPLE 23

| Active ingredient according to Example 11 | 80.0% |
|---|---|
| Saccharose | 20.0% |

The composition is prepared as described in Example 21.

Composition useful for drinking (watering)

EXAMPLE 24

| Active ingredient according to Example 8 b) | 98.0% |
|---|---|
| Saccharose | 1.95% |
| Isoamyl acetate | 0.025% |
| Ethyl acetate | 0.025% |

The composition is prepared as described in Example 21.

Powder compositions

Dusts (dusting compositions)

EXAMPLE 25

| Active ingredient according to Example 4 | 90.0% |
|---|---|
| Silica gel of great surface | 8.0% |
| Saccharose | 2.0% |

The composition is prepared by mixing and then grinding the components to a particle size lower than 20 μm.

EXAMPLE 26

| Active ingredient according to Example 5 | 90.0% |
|---|---|
| Silica gel of great surface | 8.0% |
| Saccharose | 2.0% |

The composition is prepared as described in Example 25.

EXAMPLE 27

| Active ingredient according to Example 9 | 90.0% |
|---|---|
| Talc | 9.0% |
| Saccharose | 1.0% |

The composition is prepared as described in Example 25 with a particle size lower than 20 μm.

EXAMPLE 28

| Active ingredient according to Example 6 | 50.0% |
|---|---|
| Silica gel of great surface | 10.0% |
| Talc | 35.0% |
| Saccharose | 5.0% |

The composition is prepared as described in Example 25.

EXAMPLE 29

| Active ingredient according to Example 7 | 50.0% |
|---|---|
| Silica gel of great surface | 10.0% |
| Talc | 35.0% |
| Saccharose | 5.0% |

The composition is prepared as described in Example 25.

EXAMPLE 30

| Active ingredient according to Example 12 | 50.0% |
|---|---|
| Silica gel of great surface | 10.0% |
| Talc | 35.0% |
| Saccharose | 5.0% |

The composition is prepared as described in Example 25.

Wettable powders (WP compositions)

EXAMPLE 31

| Active ingredient according to Example 4 | 95.0% |
|---|---|
| Silica gel of great surface | 4.0% |
| Sodium N-methyltaurimide | 1.0% |

The composition is prepared by homogenizing the components and then grinding the mixture obtained to a particle size lowe than 40 μm.

EXAMPLE 32

| Active ingredient according to Example 5 | 95.0% |
|---|---|
| Silica gel of great surface | 4.0% |
| Sodium N-methyltaurimide | 1.0% |

The composition is prepared as described in Example 31.

EXAMPLE 33

| Active ingredient according to Example 6 | 95.0% |
|---|---|
| Kaolin | 4.0% |
| Sulfite waste powder | 0.5% |
| $C_{6-9}$ fatty alcohol sulfate sodium salt on a silica gel carrier of great surface | 0.5% |

The composition is prepared as described in Example 31.

EXAMPLE 34

| Active ingredient according to Example 7 | 95.0% |
|---|---|
| Kaolin | 4.0% |
| Sulfite waste powder | 0.5% |
| $C_{6-9}$ fatty alcohol sulfate sodium salt on a silica gel carrier of great surface | 0.5% |

The composition is prepared as described in Example 31.

EXAMPLE 35

| Active ingredient according to Example 9 | 98.0% |
|---|---|
| Saccharose | 0.5% |
| Silica gel of great surface | 1.0% |

-continued

| | |
|---|---|
| Polyoxyethylene sorbitan monooleate | 0.5% |

The composition is prepared as described in Example 31.

EXAMPLE 36

| | |
|---|---|
| Active ingredient according to Example 12 | 99.5% |
| Polyoxyethylene sorbitan monooleate | 0.5% |

The composition is prepared as described in Example 31.

Aerosol composition

EXAMPLE 37

| | |
|---|---|
| Active ingredient according to Example 11 | 40.0% |
| Saccharose | 3.0% |
| Nonylphenol polyglycol ether (EO = 10) | 0.1% |
| Lecithin | 1.0% |
| Isoamyl acetate | 0.1% |
| Butyl acetate | 0.1% |
| Carrier gas | 55.7% |

The composition is prepared in such a way that saccharose, surface active agents and attractants are dissolved in the active ingredient under stirring, then the liquid obtained is filled into aerosol bottles. The bottle is closed together with the valve, filled with the carrier gas and finally, the nozzle is placed onto the bottle.

Biological efficiency

EXAMPLE 38

Three families of bees, being present in good condition on nine frames, were infected with 'Varroa jacobsoni' to a medium extent, then treated three times, on every third day with the cell-free fermentation broth prepared as described in Example 8 a). Each time, 60 ml of the cell-free fermentation broth prepared as described in Example 8 a) was evenly sprayed by using an airpump spraying device on the honeycomb surfaces and the bees swarming on such surfaces. In addition, each bee family was exposed to the effect of a smoking strip containing 30 mg of amitrase active agent (ANTIVAR for veterinary use) on the third day after the last treatment.

Three other bee families used as control were treated only with ANTIVAR (30 mg of amitrase) in the periods of treatments by the fermentation broth prepared in Example 8 a). Then the number of perished mites and bees inside the hive was counted and registered. Also, the general condition and behavior of the families and the queen-bee were observed.

Test conditions

Bee-hives equipped with mite-collecting trays

A tray made of aluminum and provided with a 5 mm high folded rim was placed on the floor-plate of the bee-hives. In case of necessity, the tray could be removed or replaced through an appropriately shaped opening made in the plane of the floor-plate, without the need to open the bee-hive itself.

Determination of the number of bees, larvae and pupae died inside the bee-hive

The number of bees, larvae and pupae died inside the bee-hive was checked every day, by using a trap, i.e. a box made of aluminum which was open at its upper and lower side and equipped with a sliding tray at the bottom. The upper opening was covered with a wire mesh containing 8 mm holes in order to prevent the bees from carrying dead mites from the bee-hive.

The live bees could leave the bee-hive through the wire mesh only if they did not carry any burden, thus the number of the dead individuals could be determined at any time. The open lower side of the trap joined directly to the exit of the bee-hive.

Behavior of the bee families

The behavior, i.e. the humming and murmuring of bee families, location and motion on the surface of the frames and the behavior of individual bees were observed by visual inspection in periods of opening the bee-hives and lifting the frames therefrom.

Health condition and behavior of the queen-bees

Health condition and behavior of the queen-bees were checked by visual inspection. Such observation was extended to monitoring the behavior of bees forming the "court" of the queen-bee, the queen-bee's motions, the soundness of her wings (e.g. insect-bitten edges) and her way of searching for the cells suitable for laying eggs was also observed in order to draw appropriate conclusions concerning the activity of the queen-bee.

Determination of inhabited strips on the honeycomb

Under the term of "inhabited strip of the honeycomb" we mean the area stretching between two adjacent sections of the honeycomb was meant where at least 70 to 80% of opposite surfaces of the honeycomb were covered by bees.

Carrying out of the investigation

By each treatment, 60 ml of cell-free undiluted fermentation broth, prepared as described in Example 8a) and kept at room temperature, were sprayed by using a manually operated air-jet device onto the entire surface of nine frames holding three families of bees (i.e. onto a surface of 27 216 $cm^2$ per family). The bees covered the honeycomb surface quite evenly during the spraying. The smoking strip containing the amitrase active agent (ANTIVAR) used as control was bent in a "V"-form and placed onto the aluminum tray, then lit and pushed inside the bee-hive. The exit opening was kept closed for one hour.

Test parameters a) The number of perished mites was registered in the 24th, 48th and 72nd hour after treatments.

b) The number of perished bees was counted and registered in every third day, before the beginning of treatments.

c) The behavior of the families and the queen-bee as well as the number of inhabited strips of the honeycombs were checked at the time of treatments when the bee-hives were opened.

Results

Number of perished Varroa jacobsoni mites each per bee family after treatments carried out every 3rd day, 3 times altogether by using the cell-free fermentation broth prepared as described in Example 8a) followed by a treatment with amitrase

| Treatment | Time elapsed after treatment (hours) | Number of perished mites in the bee family No. | | |
|---|---|---|---|---|
| | | 1 | 2 | 3 |
| 1 | 24 | 74 | 43 | 31 |
| | 48 | 5 | 12 | 10 |
| | 72 | 1 | 1 | 0 |
| | Total: | 80 | 57 | 41 |
| 2 | 24 | 47 | 52 | 34 |
| | 48 | 6 | 1 | 3 |
| | 72 | 0 | 1 | 1 |
| | Total: | 53 | 54 | 38 |
| 3 | 24 | 62 | 77 | 47 |
| | 48 | 12 | 9 | 7 |
| | 72 | 2 | 0 | 1 |
| | Total: | 76 | 86 | 55 |
| | Grand total: | 209 | 197 | 134 |
| 4 amitrase (30 mg) | 24 | 225 | 134 | 94 |
| | 48 | 24 | 4 | 11 |
| | 72 | 0 | 1 | 0 |
| | Total: | 249 | 139 | 105 |

Number of perished "*Varroa jacobsoni*" mites each per bee family after treatment in every third day, 4 times altogether by using 30 mg of amitrase per treatment (control)

| Treatment | Time elapsed after treatment (hours) | Number of perished mites in the bee family No. | | |
|---|---|---|---|---|
| | | 1 | 2 | 3 |
| 1 | 24 | 164 | 241 | 190 |
| | 48 | 3 | 12 | 3 |
| | 72 | 0 | 1 | 0 |
| | Total: | 167 | 254 | 193 |
| 2 | 24 | 68 | 87 | 37 |
| | 48 | 0 | 3 | 1 |
| | 72 | 0 | 1 | 0 |
| | Total: | 68 | 91 | 38 |
| 3 | 24 | 21 | 35 | 24 |
| | 48 | 0 | 2 | 1 |
| | 72 | 0 | 0 | 2 |
| | Total: | 21 | 37 | 27 |
| 4 | 24 | 57 | 55 | 32 |
| | 48 | 4 | 0 | 4 |
| | 72 | 1 | 0 | 1 |
| | Total: | 62 | 55 | 37 |

Perishment of bees

The number of dead bees found in the traps corresponded to the normal mortality rates. Accordingly, the treatments did not cause any significant increase in the number of dead bees.

Behavior of the bee families and queen-bee, number of inhabited strips

No pathological change was experienced in the general condition of the bee families and queen-bee on effect of the same impression concerning the general condition of the families.

EXAMPLE 39

Toxicological examination on bees

Oral $LD_{50}$ value on *Apis mellifera* of the cell-free fermentation broth prepared according to Example 8a)

Test material

A concentration-halving serial dilution was prepared from the cell-free fermentation broth of Example 8a) with the solution described hereinafter to give a first concentration of 1.00% and a final concentration of 0.25% in the series (calculated for the fermentation broth).

Components of the solution were as follows:
granulated sugar 20.0 g
acetone 5.0 ml
distilled water ad 100 ml An 0.2 ml dose of each solution of the series was given to groups consisting of 10 bees each.

Dosage 500.0, 1000.0 and 2000.0 micrograms per 10 bees contained in 0.2 ml solution.

Test animals

Bees used for the tests were taken by carefully sweeping them from the frames used to rearing. The bees were sampled from three families being in good physical condition, in the period of intensive swarming out. The test bees according to different families were placed in separate plastic boxes equipped with a perforated lid.

For the testing of each dose, 6 groups of 10 bees each were formed by allocating individuals from each family to 2 groups.

Method of investigation

The test animals swept from the frames used for rearing were delivered immediately to the laboratory where they were narcotized with carbon dioxide gas. The groups consisting of 10 bees each, were placed into a 10 cm high, 5 cm diameter cylinder made of wire mesh with 4 mm holes galvanized with zinc and closed at one end with aluminum foil and at the other end with a cork plug wrapped in aluminum foil.

In the middle of the cork plug, a hole of 1 cm in diameter, 0.4 mm in depth with 0.5 ml capacity was prepared to provide a feeding place. This hole was spanned with thin wires placed with a spacing of 3 to 4 mm.

One hour after narcotizing the bees with carbon dioxide gas, 0.2 ml solution containing the defined dose of the cell-free fermentation broth prepared as described in Example 8a) was administered by using a glass syringe to the feeding points of the 6 test groups.

Each of the 6 control groups were given 0.2 ml of empty sugar solution each. By four hours after the first feeding, the bees consumed the first portion. Then, in every third hour they were given the sugar syrup ad libitum.

In addition to the 1 hour period of starving, the uniform rate of consumption of the test food was assured by a known inherent property of the bees, namely that they feed each other by an even distribution of the feed.

During the observation period, the laboratory was darkened and only a dim light was used by the staff during the periods of feeding. Furthermore, the room was used exclusively for nothing but this experiment. A constant 23° to 24° C. temperature and 55 to 70% humidity was maintained throughout the test period; both parameters were checked and registered in every three hours.

Evaluation

The mortality was observed by 4, 24 and 48 hours after giving the sugar syrup that contained the test material. Since the occurance of perishment is a natural phenomenon among bees torn away from their natural habitat (mainly for the reason that they sting each other to death in over-excitement caused by the sudden change of the environment), lethality rates registered at different dose levels were corrected according to the average mortality rates of the control groups and the corrected figures were taken into consideration to the purpose of further evaluations. The results are summarized in the Table.

5 to 10 ml of solution containing the fermentation broth prepared as described in Example 3b) were given into the feeding hole by using a glass syringe and allowed to the bees ad libitum.

During the observation period, the laboratory was completely darkened and the room was used for no other purposes. A constant temperature of 23°–24° C. and humidity of 55 to 70% were maintained throughout the test.

Results
Mortality of *Apis mellifera* during determination of the oral $LD_{50}$ value of the cell-free fermentation broth prepared as described in Example 8 a)

| DOSE: quantity of the drug added to 0.2 ml of sugar syrup and given to a group of 10 bees at each time (microgram/10 bees) | Concentration of fermentation broth in the sugar syrup % by wt/vol | Serial number of the groups consisting of 10 bees each | Number of perished bees per group 4 / 24 / 48 hours after the first feeding | Average number of perished bees out of every 10 bees, during 48 hours | Corrected mortality % |
|---|---|---|---|---|---|
| 500.0 | 0.25 | 1 | 0 0 0 | 0.67 | 0.00 |
|  |  | 2 | 0 0 0 |  |  |
|  |  | 3 | 0 1 2 |  |  |
|  |  | 4 | 1 1 1 |  |  |
|  |  | 5 | 0 0 1 |  |  |
|  |  | 6 | 0 0 0 |  |  |
| 1000.0 | 0.50 | 1 | 0 1 1 | 0.83 | 1.79 |
|  |  | 2 | 0 0 0 |  |  |
|  |  | 3 | 0 0 2 |  |  |
|  |  | 4 | 0 0 0 |  |  |
|  |  | 5 | 0 0 1 |  |  |
|  |  | 6 | 0 0 1 |  |  |
| 2000.0 | 1.00 | 1 | 0 1 2 | 1.00 | 3.57 |
|  |  | 2 | 0 0 0 |  |  |
|  |  | 3 | 2 0 2 |  |  |
|  |  | 4 | 0 0 0 |  |  |
|  |  | 5 | 0 1 1 |  |  |
|  |  | 6 | 0 1 1 |  |  |
| CONTROL | 0.00 | 1 | 1 1 1 | 0.67 | — |
|  |  | 2 | 0 0 0 |  |  |
|  |  | 3 | 0 0 0 |  |  |
|  |  | 4 | 0 0 2 |  |  |
|  |  | 5 | 0 1 1 |  |  |
|  |  | 6 | 0 0 0 |  |  |

From the above data it can be stated that the oral $LD_{50}$ value is higher than 200.0 microgram/bee, i.e. higher than 2.0 g/kg of body weight of bee. (The $LD_{50}$ value of amitrase is 12 microgram/bee.)

EXAMPLE 40

Investigation of the acaricidal effect of the fermentation broth prepared according to Example 3b) on *Apis mellifera* infected by the great Asian mite (*Varroa jacobsoni*)

Test material

A 2.5% solution of the fermentation broth prepared as described in Example 3b) by using a sugar syrup of 50% concentration.

Test animals

Bees used for the test were taken by carefully sweeping them from the frames used for rearing from a family being in good condition, in the period of intensive swarming out. The test bees were placed in a plastic box equipped with a perforated lid.

Method of investigation

The animals swept from the frames used for rearing were immediately delivered to the laboratory where they were narcotized with carbon dioxide gas. The doped bees were examined under a magnifying lens and individuals infected with mites were placed in a 10 cm high, 8 cm diameter cylinder made of wire mesh with 4 mm holes and covered with aluminum foil at one end. A 3 to 5 cm long empty strip of honeycomb was fixed to the bottom of the cylinder.

Evaluation

The perished mites remaining on the bees were counted by 12 hours after administration of the sugar syrup containing the test material, after narcotizing the bees with gaseous carbon dioxide. It was found that all the mites being present on the bees perished and fell to the bottom of the cage.

Thus, by feeding the sugar syrup containing the fermentation broth prepared as described in Example 3b), an effectivity of 100% was achieved within 12 hours.

We claim:

1. A biologically pure culture of the bacillus strain deposited at the National Collection of Agricultural and Industrial Microorganisms, Budapest, Hungary under the identification No. 001083, which forms mat, greyish colonies of 1 to 2 mm in diameter on a simple nutrient agar and shows the following properties:

| | |
|---|---|
| a) Gram: | positive, |
| b) sporulation: | oval, |
| c) motion: | positive, |
| d) anaerobic growth: | positive, |
| e) growth on bismuth sulfite agar: | +/−, |
| f) growth on eosin-methylene blue agar: | +/−, |
| g) growth in the presence of 7% sodium chloride: | positive, |
| h) catalase: | positive, |
| i) $NO_3$—$NO_2$: | negative, |

-continued

| | | |
|---|---|---|
| j) Voges-Proskauer test | | negative, |
| k) indole: | | negative, |
| l) urease (kristensen): | | negative, |
| m) arginine-dihydrolase: | | negative, |
| n) lysine-decarboxylase: | | negative, |
| o) ornithine-decarboxylase: | | negative, |
| p) aesculin hydrolysis: | | positive, |
| q) starch hydrolysis: | | negative, |
| r) casein hydrolysis: | | negative, |
| s) lecithin hydrolysis: | | negative, |
| t) gelatine hydrolysis: | | positive, |
| u) ammonium citrate: | | negative, |
| ü) acid formation on the Hungh-Leifson's oxidation-fermentation nutrient medium: | | oxidative, |
| v) gas formation, peptone-water glucose: | | negative, |
| x) acid formation (BSS) | glucose: | positive, |
| | fructose: | positive, |
| | lactose: | negative, |
| | maltose: | negative, |
| | mannitol: | positive, |
| | rhamnose: | negative, |
| | saccharose: | positive |
| | xylose: | negative, |
| (peptone water) | arabinose: | negative, |
| | adonitol: | negative, |
| z) ONPG: | | positive. |

2. A culture of the combination of the bacillus strain deposited at the National Collection of Agricultural and Industrial Microorganisms, Budapest, Hungary, under the Identification Number 001083 combined with the pseudomonas strain deposited at said Collection under the Identification number 001086.

3. A process for the preparation of an acaridally active composition comprising aerobically or partially anaerobically fermenting a combination of the bacillus strain deposited at the National Collection of Agricultural and Industrial Microorganisms, Budapest, Hungary, under the Identification Number 001083 and the pseudomonas strain deposited at said Collection under the Identification number 001086 in a liquid nutrient medium containing carbohydrate and inorganic nitrogen.

4. A process for the preparation of an acaridally active composition comprising aerobically partially anaerobically fermenting the bacillus strain deposited at the National Collection of Agricultural and Industrial Microorganisms, Budapest, Hungary, under the Identification Number 001083 in a liquid nutrient medium containing carbohydrate and inorganic nitrogen.

5. An acaricidal composition, which comprises as the active ingredient, an acaricidally effective amount of:

the fermentation broth or cell-free fermentation broth of 1) the bacillus strain deposited at the National Collection of Agricultural and Industrial Microorganisms, Budapest, Hungary, under the Identification Number 001083, or 2) said bacillus strain in combination with the pseudomonas strain deposited at said Collection under the Identification number 001086, and at least one solid or liquid inert carrier, wherein said fermentation broth or cell-free fermentation broth may be present as a concentrate or in dried powder form.

6. An acaricidal process for the protection of *Apis millifera* against *Varroa jaoobsoni*, comprising applying to *Apis mellifera* or their surrounding loci an acaricidally effective amount of the acaricidal composition of claim 5.

7. The process of claim 6 wherein the surrounding loci of *Apis mellifera* is the hive or frames of the hive and wherein the acaricidal composition is concentrated, dried into a powder, diluted or sterilized.

8. The process of claim 7 wherein the surrounding loci of *Apis millifera* is their food source or drinking water.

9. An acaricidal process for the protection of *Apis millifera* against *Varroa jaoobsoni*, comprising the step of treating *Apis mellifera* or their surrounding loci with an acaricidally effective amount of an acaricidal composition comprising an acaricidally effective amount of:

the fermentation broth or cell-free fermentation broth of the pseudomonas strain deposited at the National Collection of Agricultural and Industrial Microorganisms, Budapest, Hungary, under the Identification number 001086, wherein said fermentation broth or cell-free fermentation broth may be present in as a dried powder, diluted or sterilized.

* * * * *